US00PP16909P3

(12) United States Plant Patent

Lim et al.

(10) Patent No.: US PP16,909 P3

(45) Date of Patent: Aug. 1, 2006

(54) SHRUB ROSE PLANT NAMED 'BAIORE'

(50) Latin Name: *Rosa hybrida*
Varietal Denomination: BAIore

(75) Inventors: Peter P. Lim, Yamhill, OR (US); Jerry Twomey, Leucadia, CA (US)

(73) Assignee: Bailey Nurseries, Inc., St. Paul, MN (US)

( * ) Notice: Subject to any disclaimer, the term of this patent is extended or adjusted under 35 U.S.C. 154(b) by 104 days.

(21) Appl. No.: 11/023,163

(22) Filed: Dec. 28, 2004

(65) Prior Publication Data

US 2006/0143746 P1 Jun. 29, 2006

(51) Int. Cl.
*A01H 5/00* (2006.01)

(52) U.S. Cl. ..... Plt./107

(58) Field of Classification Search ..... Plt./102, Plt./107

See application file for complete search history.

*Primary Examiner*—Howard J. Locker
(74) *Attorney, Agent, or Firm*—Buchanan Ingersoll PC

(57) ABSTRACT

A new and distinct variety of landscape shrub rose plant is provided which abundantly forms on a substantially continuous basis attractive single medium pink blossoms that change to light pink upon maturity. The plant exhibits a dense upright and bushy growth habit and is well suited to form an informal hedge. The medium green foliage bears a satiny finish and contrasts nicely with the blossom coloration. High tolerance to Black Spot and Powdery Mildew is displayed. The plant can be grown to advantage to provide attractive ornamentation in parks and gardens.

2 Drawing Sheets

Figure 1:
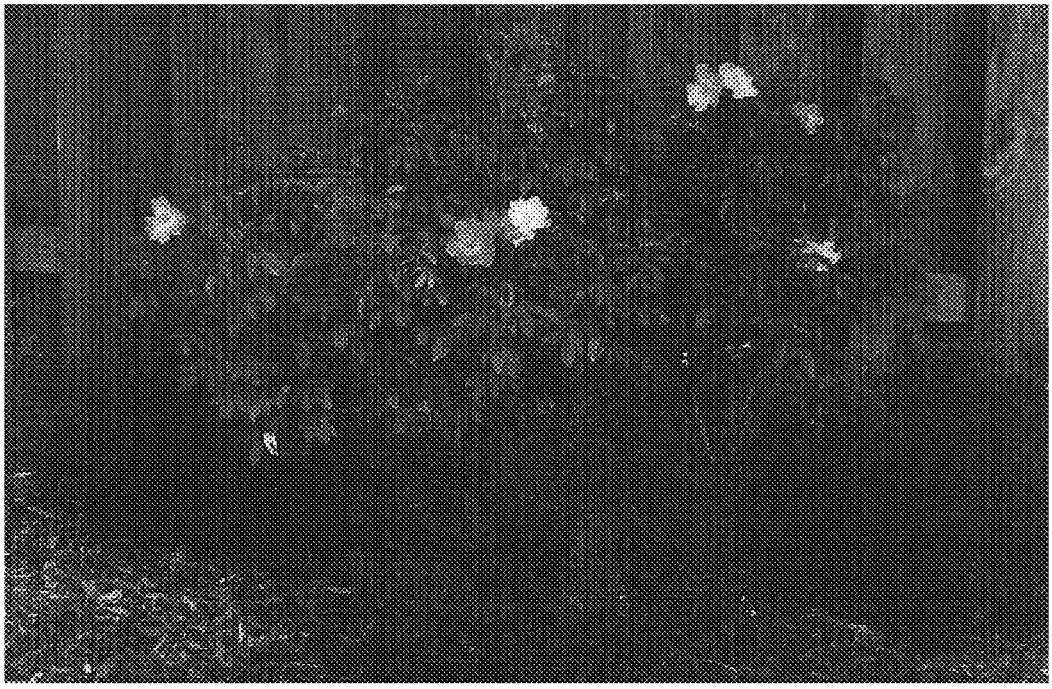

Botanical commercial classification: *Rosa hybrida*/Shrub Rose Plant.

Varietal denomination: cv. 'BAIore'.

SUMMARY OF THE INVENTION

The new variety of *Rosa hybrida* landscape shrub rose plant was created at Yamhill, Oreg., U.S.A., during 1991 by artificial pollination wherein two parents were crossed which previously had been studied in the hope that they would contribute the desired characteristics. The female parent (i.e., the seed parent) was the hybrid *Rosa rugosa* 'Schneezwerg' variety (non-patented in the United States). The 'Schneezwerg' variety sometimes is known as the 'Snow Dwarf' variety. The male parent (i.e., the pollen parent) was the hybrid *Rosa kodesii* 'Champlain' variety (non-patented in the United States). The parentage of the new variety can be summarized as follows:

'Schneezwerg'×'Champlain'.

The seeds resulting from the above pollination were sown and plants were obtained which were physically and biologically different from each other. Selective study resulted in the identification during 1994 of a single plant of the new variety having the distinctive ornamental characteristics hereafter described.

It was found that the new variety of the present invention:

(a) exhibits a dense upright and bushy growth habit, (b) abundantly forms on a substantially continuous basis attractive single medium pink blossoms that change to light pink upon maturity, (c) forms medium green foliage with a satin aspect, (d) displays high tolerance to Black Spot and Powdery Mildew; and (e) is particularly well suited for growing as attractive ornamentation in parks and gardens.

The medium pink blossoms that initially are formed assume a blend of pale pink tints prior to petal drop. The blossom coloration contracts nicely with the satiny medium green foliage. The new variety performs well in U.S.D.A. Hardiness Zone Nos. 4 to 9.

The new variety well meets the needs of the horticultural industry. It can be grown to advantage where attractive ornamentation is desired, such as in parks and gardens. The upright growth habit is well suited to form an informal hedge.

The new variety can be readily distinguished from other varieties including its parental varieties. More specifically, the 'Schneezwerg' forms white blossoms having approximately 12 to 16 petals and dark green foliage, and the 'Champlain' variety forms dark red blossoms having approximately 30 petals.

The new variety has been found to undergo asexual propagation by budding on an understock beginning in August 1992 and by the rooting of cuttings. 'Dr. Huey' rootstock was used during the budding. Such asexual propagation by these techniques at Yamhill, Oreg., U.S.A., St. Paul, Minn., U.S.A., and at Phoenix, Ariz., U.S.A., has shown that the characteristics of the new variety are stable and are strictly transmissible by such asexual propagation from one generation to another. Accordingly, the new variety reproduces true to type. The new variety grows well on its own roots.

Initially the new plant was designated 91H1, and was evaluated during 1999 and 2000 under the designation 99RR507. The new variety subsequently has been named the 'BAIore', and currently is being marketed while using the NORTHERN ENCORE trademark.

BRIEF DESCRIPTION OF THE PHOTOGRAPHS

The accompanying photographs show as nearly true as it is reasonably possible to make the same in color illustrations of this character, typical specimens of the new variety. The rose plants of the new variety had been propagated by the rooting of cuttings, were approximately two and three years of age, and were being grown outdoors at St. Paul, Minn., U.S.A. and Yamhill, Oreg., U.S.A. during the 2003 and 2004 seasons.

Figure 2:
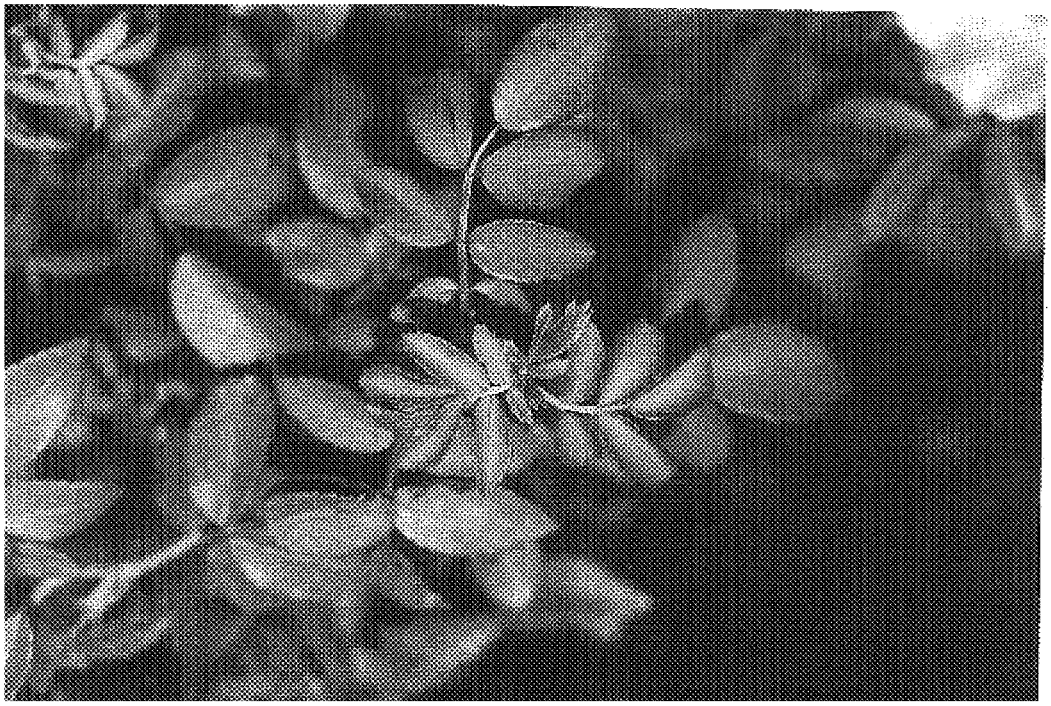
Figure 3:
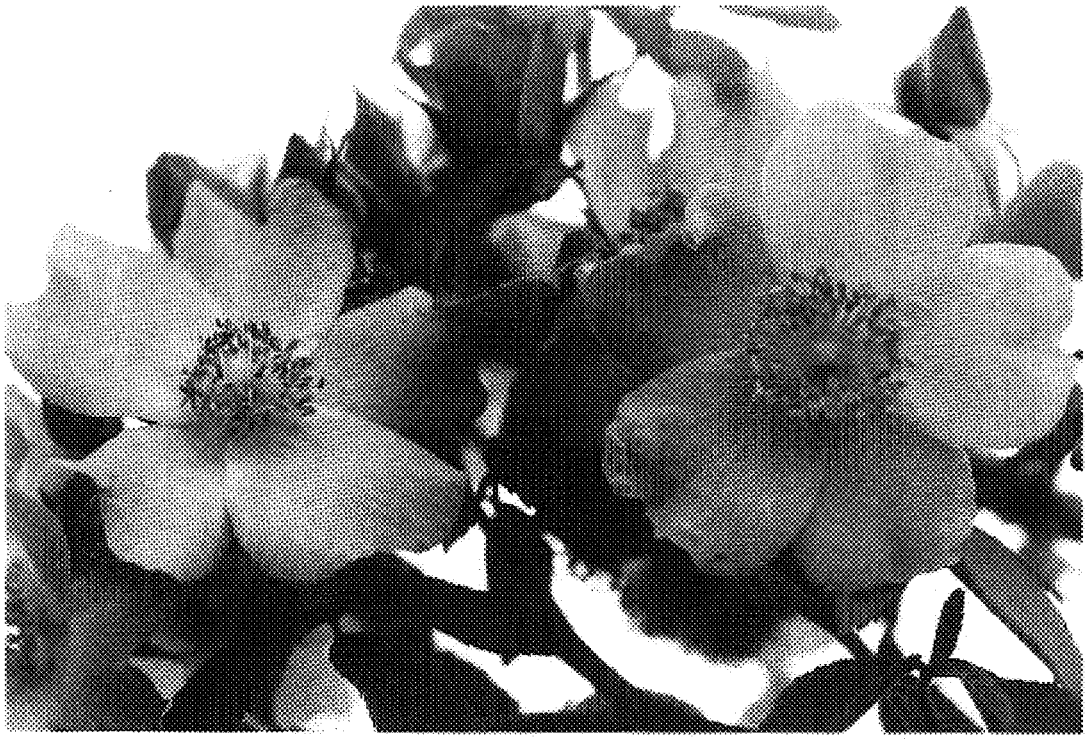
Figure 4:
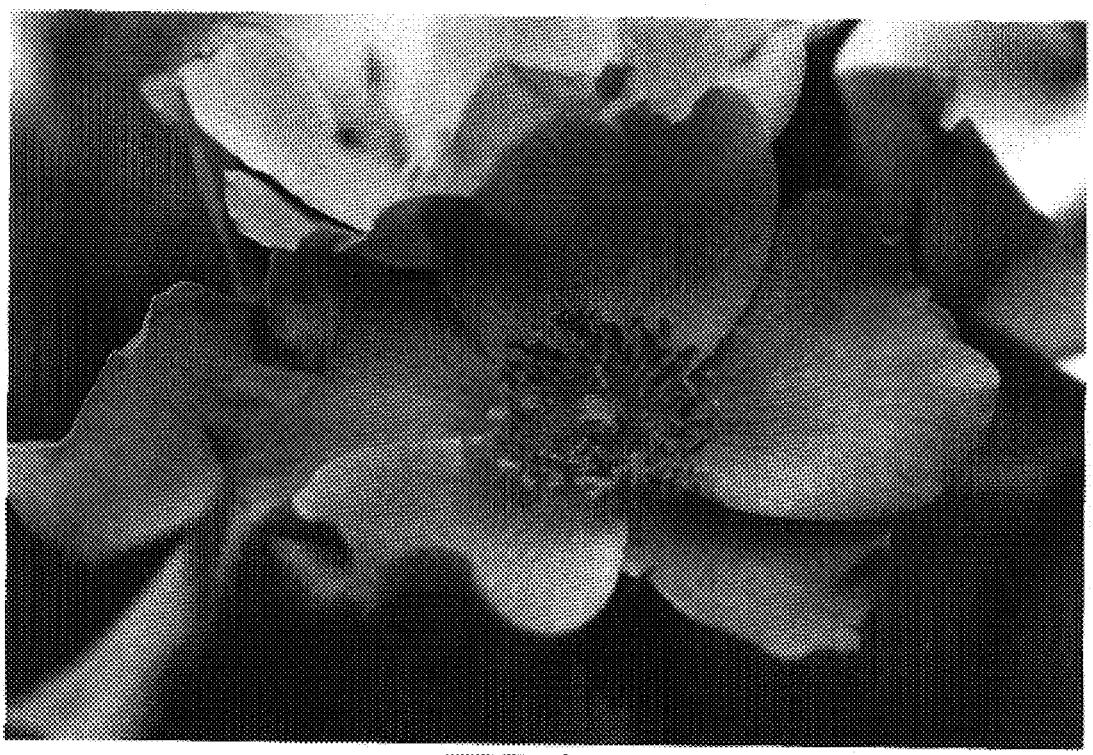

FIG. 1 illustrates an overall view of a plant of the new variety while growing in a garden setting. Blossoms are present in various stages of maturity, FIG. 2 illustrates a close view of the medium green foliage, FIG. 3 illustrates a close view of a cluster of typical single blossoms of the new variety, and FIG. 4 illustrates a further close view of a cluster of the attractive single blossoms of the new variety.

DETAILED DESCRIPTION

The chart used in the identification of the colors is that of The Royal Horticultural Society (R.H.S. Colour Chart). Common color terms are to be accorded their ordinary dictionary significance. The description is based on the observation of two and three year-old plants while grown outdoors on their own roots during June 2003 at Yamhill, Oreg., U.S.A., and July 2004 at St. Paul, Minn., U.S.A.

Botanical classification: *Rosa hybrida*, var. 'BAIore'.
Class: Landscape Shrub.
Plant:
- *Height*.—Approximately 1.25 cm to 2 m on average at the end of the growing season.
- *Width*.—Approximately 90 cm to 1.25 m on average at the end of the growing season.
- *Habit*.—Bushy, upright and spreading.

Branches:
- *Color*.—Young stems: Yellow-Green Group 144B with highlights of Greyed-Purple Group 184B with some pubescence. Adult wood: Yellow-Green Group 144B and 144C.
- *Thorns*.—Size: commonly approximately 1 to 1.25 cm in length on average together with some smaller pirckles commonly near the peduncle. Color: Yellow-Green Group 144B with highlights of Greyed-Purple Group 185B.

Leaves:
- *Stipules*.—Generally parallel with the auricle facing outward.
- *Petioles*.—Upper surface: Red-Purple Group 59C with highlights of Yellow-Green 147C. Under surface: commonly between Yellow-Green Group 148B and 148C with highlights of Red-Purple Group 60B.
- *Leaflets*.—Number: 3, 5 (most often), and 7. Shape: ovate with a rounded base and an acuminate tip. Margin: serrulate. Texture: bears a satiny finish. General appearance: medium green with a satiny surface when mature. Color (young foliage): Upper surface: Green Group 138A with highlights of Red-Purple Group 59A at the margins. Under surface: Red-Purple Group 59B and Red-Purple Group 60B with highlights of Green Group 137D at the center. Color (adult foliage): Upper surface: Green Group 137B. Under surface: between Green Group 137C and 137D.

Inflorescence:
- *Number of flowers*.—Typically in clusters, and commonly approximately 13 flowers on average per stem.
- *Peduncle*.—Green Group 143A in coloration.
- *Sepals*.—Upper surface: Green Group 139C with some pubescence. Under surface: Green Group 138A mottled with Greyed-Purple Group 184B. Size: approximately 1.75 cm in length on average.
- *Buds*.—Shape: pointed as shown in FIG. 3. Size: medium. Length: approximately 1.65 cm on average. Diameter: approximately 1.0 cm on average. Color: Upper petal surface: Red-Purple Group 63B. Under petal surface: Red-Purple Group 63A.
- *Flower*.—Shape: single. Diameter: approximately 5.0 cm on average. Color (when opening begins): Upper surface: commonly between Red-Purple Group 62B and Red-Purple Group 63D with highlights of Red-Purple Group 63C. Under surface: Red-Purple Group 63C with highlights of Red-Purple Group 63B. Color (when blooming): Upper surface: Red-Purple Group 62C with highlights of Red-Purple Group 65B. Under surface: between Red-Purple Group 62C and Red-Purple Group 62D with streaks of Red-Purple Group 62A and 62B. Color (at end of blooming): Upper surface: Red-Purple Group 62D with highlights of Red-Purple Group 65A and Red-Purple Group 65B. Under surface: Red-Purple Group 65D with highlights of Red-Purple Group 65B and Red-Purple Group 65C. Color (basal petal spot): White Group 155C with streaks of Greyed-White Group 160D. Fragrance: light spice. Lasting quality: the blossoms commonly last approximately 3 to 5 days on average depending upon the temperature and sunlight exposure. Petal number: commonly 5. Petal shape: wedge-shaped commonly with a curled apex. Petal drop: commonly the petals detach cleanly at full blossom maturity. Anthers: Yellow-Orange Group 17C. Stamen number: commonly approximately 77 on average. Filament color: between Greyed-Orange Group 163B and Greyed-Orange Group 163C. Pistils: approximately 20 on average. Stigmas: Yellow-Green Group 151C in coloration. Styles: Yellow-Green Group 154B and Yellow-Green Group 154C. Receptacle: separate and free with achenes at the bottom and center.

Development:
- *Vegetation*.—Vigorous and bushy.
- *Blooming*.—Substantially continuous and everblooming during the summer months.
- *Resistance to diseases*.—Highly tolerant to Black Spot and Powdery Mildew.
- *Hardiness zone*.—U.S.D.A. Hardiness Zone Nos. 4 to 9.

We claim:

1. A new and distinct landscape shrub rose plant characterized by the following combination of characteristics:

(a) exhibits a dense upright and bushy growth habit, (b) abundantly forms on a substantially continuous basis attractive single medium pink blossoms that change to light pink upon maturity, (c) forms medium green foliage with a satin aspect, (d) displays high tolerance to Black Spot and Powdery Mildew; and (e) is particularly well suited for growing as attractive ornamentation in parks and gardens;

substantially as herein shown and described.

* * * * *